United States Patent [19]

Levine

[11] Patent Number: 5,086,765
[45] Date of Patent: Feb. 11, 1992

[54] NEBULIZER

[76] Inventor: Walter Levine, 6948 N. Keating, Lincolnwood, Ill. 60646

[21] Appl. No.: 575,146

[22] Filed: Aug. 29, 1990

[51] Int. Cl.$^5$ .............................................. A61M 11/02
[52] U.S. Cl. ........................... 128/200.21; 128/200.14; 128/911; 128/912; 128/203.12
[58] Field of Search ....................... 128/200.21, 200.14, 128/203.12, 911, 912

[56] References Cited

U.S. PATENT DOCUMENTS

| | | | |
|---|---|---|---|
| 3,762,409 | 10/1973 | Lester | 128/200.14 |
| 4,253,468 | 3/1981 | Lehmbeck | 128/200.21 |
| 4,598,704 | 7/1986 | Bordoni et al. | 128/200.14 |
| 4,938,210 | 7/1990 | Shene | 128/200.23 |

OTHER PUBLICATIONS

"Administering NebuPent TM with the Respirgard TM II Nebulizer System", Lyphomed, Inc., Publication NebuPent-008, Jun., 1989.

Primary Examiner—Edgar S. Burr
Assistant Examiner—Lisa Malvaso

[57] ABSTRACT

A nebulizer for use in administering medication to a patient includes a tubular body having opposed ends, a central portion defined by one-way valves and having a vial attached thereto, a nebulizer jet device disposed in the vial and including a multiple baffle arrangement configured to deliver a substantial amount of optimally-sized aerosol particles to a patient through inhalation at one of the tubular ends.

18 Claims, 2 Drawing Sheets

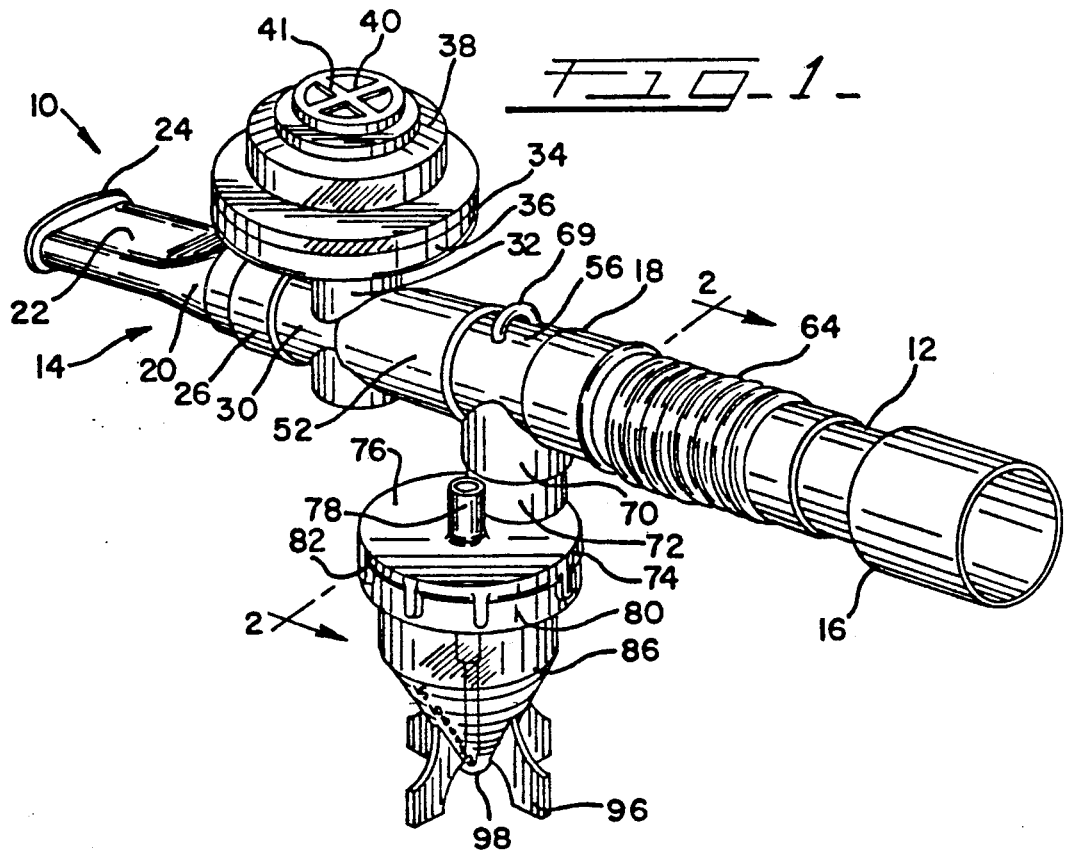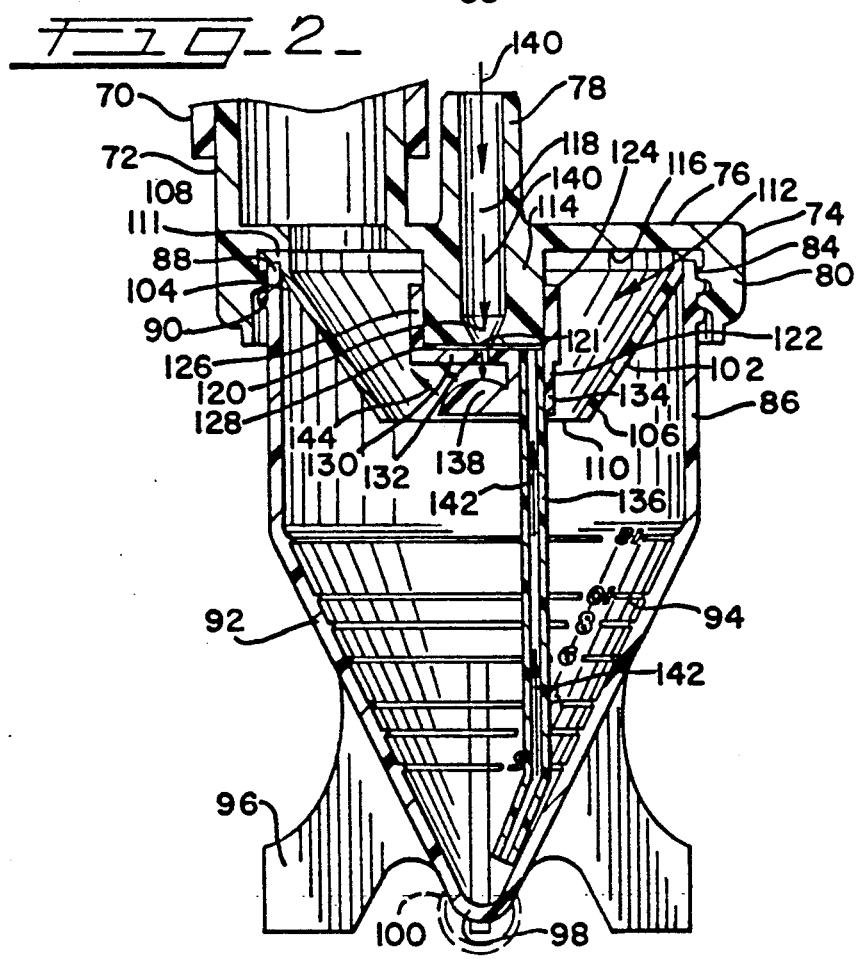

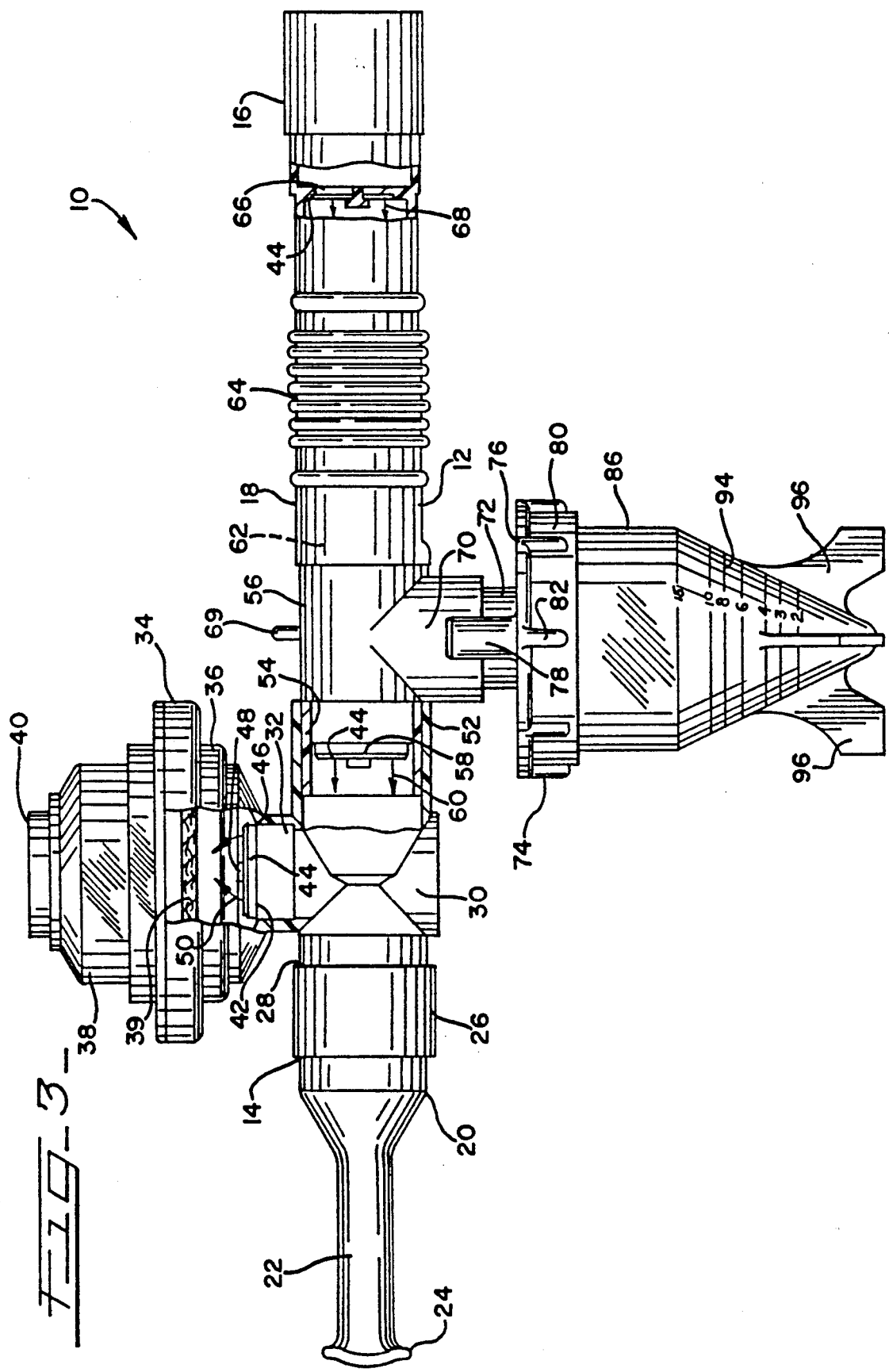

NEBULIZER

BACKGROUND OF THE INVENTION

The present invention relates generally to respiratory treatment devices, and specifically to nebulizers used for administering medication to a patient through respiration.

One rapidly developing area of respiratory treatment involves the administration of aerosolized medication to patients with toxic respiratory conditions through the use of nebulizers. A significant design consideration in developing such treatment systems is the prevention of environmental contamination from toxic elements which may be exhaled by the patient during treatment. Another factor in the treatment of patients with toxic respiratory conditions is that often the medication used is itself toxic, or causes unwanted side effects, to the patient and/or to attending health care personnel.

In view of the above factors, the goal in the nebulization of such toxic medications is to optimize the delivery of the medication to the alveoli, while minimizing the deposition of the medication in the patient's airways. Research has indicated that optimum alveolar deposition depends on the size of the nebulized particles. Particle size is a function of nebulizer type, baffling, and gas pressure. Particles larger than 2 microns result in increased bronchial and decreased alveolar deposition. On the other hand, a particle size of less than 1 micron can result in nonlocalized deposition anywhere in the pulmonary tree, but in most cases, these smaller particles are exhaled without performing a therapeutic function. Thus, the preferred particle size falls in the range of 1-2 microns, with an optimal particle size being 2 microns, plus or minus 0.5 micron.

Studies of conventional nebulizers have found that some nebulizers emit smaller-sized particles (less than 1 micron), and consequently do not deliver an adequate amount of medication to the patient. On the other hand, other nebulizers deliver more medication to the patient; however these latter devices generate larger particles. There has been some concern as to the size of the particles generated by these latter nebulizers, and to the consequential increased chance of patient bronchial distress.

As an example, prior to 1979, when the first cases of acquired immune deficiency syndrome (AIDS) were reported, physicians in the United States saw fewer than 100 cases of *Pneumocystis carinii* pneumonia (PCP) per year. Those cases occurred in patients whose immune systems were compromised due to other factors, such as disease or surgery. During that time, PCP was a treatable and preventable disease which responded well to pentamidine isethionate (pentamidine), a liquid bronchodilator medication. However, when pentamidine is used to treat PCP in AIDS patients, the resulting toxicity of the medication and resulting side effects, such as bronchial irritation and/or severe coughing, discouraged further use of this medication.

Recent studies have shown that pentamidine can be used as a prophylaxis in AIDS patients who have a high risk of developing PCP. The pentamidine has been found to be most effective when administered to the patient through a nebulizer, rather than intravenously. Also, the nebulizer has been found to reduce contamination. However, tests of conventional nebulizers have shown that in many cases, adequate amounts of pentamidine are not reaching the alveoli, but instead are being deposited in the bronchial tubes.

Thus, there is a need for a nebulizer which consistently produces an aerosol of medication comprised of a large percentage of particles in the range of 1-2 microns, while optimizing the delivery of the medication to the patient's alveoli.

SUMMARY OF THE INVENTION

Accordingly, the nebulizer of the invention is designed to consistently generate a large percentage of particles in the range of 1-2 microns, and to facilitate the optimum utilization of medication by the patient. This is accomplished in large part by the provision of multiple baffles in the nebulizing portion of the device.

More specifically, the present nebulizer includes a tubular body having an inspiratory end portion, an air inlet end portion and a central portion disposed between the inspiratory and the inlet end portions; one-way valve devices for controlling the flow of air, oxygen, aerosols or other fluids through the central portion from the inspiratory and the inlet end portions; a vial configured for connection to the tubular body and being in fluid communication with the central portion, the vial adapted to retain a supply of medicine therein; and a nebulizer jet mechanism for creating an aerosol of fine micron-size particles of the medicine, the nebulizer jet mechanism including a plurality of baffle members and being disposed on the tubular body so as to be in fluid communication with the vial and the central portion.

The present nebulizer jet mechanism preferably includes a female jet member disposed in the vial and having a hemispherical baffle disposed to provide an initial fragmentation of droplets of medication into particles, and a frustoconically-shaped secondary baffle which further fragments the particles prior to their introduction into the central portion.

BRIEF DESCRIPTION OF THE DRAWINGS

FIG. 1 is a top perspective view of the nebulizer of the invention;

FIG. 2 is a fragmentary vertical sectional view taken along the line 2—2 of FIG. 1 and in the direction generally indicated; and FIG. 3 is a front elevational view of the nebulizer of FIG. 1 with portions shown cut away for clarity.

DESCRIPTION OF THE PREFERRED EMBODIMENT

Referring now to FIGS. 1 and 3, the nebulizer of the invention is generally designated 10. The nebulizer 10 includes a tubular body 12 having an inspiratory end portion 14, an opposing air inlet end portion 16, and a central portion 18 disposed therebetween. The body 12 is preferably molded of polymeric plastic, and is actually a series of components joined together in mating arrangement and fixed in position with a suitable adhesive.

At the inspiratory end 14, a mouthpiece 20 has a relatively vertically flattened portion 22 contoured for comfortable insertion into the patient's mouth. The flattened portion 22 ends in a lip 24 which is radiused for safety reasons. Opposite the lip 24, a collar 26 defines a cavity into which a first end 28 of a tubular manifold 30 is inserted. The first end 28 of the manifold 30 is in communication with an exhalatory port 32, which is integrally joined to a bacterial and viral filter 34.

The filter 34 is preferably a bi-directional, non-conductive filter of the type sold by IPI Medical Products, Inc., Niles, Ill. under the trademark FILT-R-ALL; however equivalent bacterial and viral filters are contemplated. The filter 34 includes a base 36 which is integral with the port 32, and a preferably transparent upper housing 38 which enables inspection of a filter media 39 (best seen in FIG. 3). The upper housing also includes a filter outlet 40 (best seen in FIG. 1) having protective crossbars 41 to prevent possible damage during handling.

Corresponding peripheral edges of the upper housing 38 and the media 39 are fused to the base 36 to create a seal which prevents air or bacteria from escaping. A conventional liquid bonding solvent, such as cyclohexanol is used to seal the filter 34 in this manner. The media 39 is a synthetic fibrous mat of permanent electrets, which are a non-conductive material with imbedded electrical charges. The media 39 repels water yet allows water vapor to pass through, thus preventing any increased breathing resistance.

The flow of air, carbon dioxide or other fluids between the exhalatory port 32 and the filter 34 is controlled by a one-way valve 42, which basically consists of a flap 44 of silicone rubber held against a seat 46 by a plastic brad 48. The flap 44 is designed to fold in the direction indicated by the arrows 50 in the exhalation direction in response to air flow from the body 12 through the port 32. However, the flap 44 will close against the seat 46 in response to air flow in the reverse direction.

Opposite the first end 28 of the manifold 30, a second end 52 serves as a female connector for one end 54 of a plastic tee 56. The end 54 is provided with a one-way valve 58, which is identical in construction to the valve 48 and is disposed in the tubular end 52 so that the flap 44 opens in the direction indicated by the arrows 60. Thus, fluids such as air, oxygen, and aerosols are allowed to flow from the central portion 18 towards the mouthpiece 22, but not in a reverse direction.

A second end 62 of the tee 56 is preferably connected to the air inlet end portion 16 by a section of corrugated tubing 64, also referred to as a tubing reservoir. In the preferred embodiment, the tubing 64 is transparent; however the use of opaque tubing is also contemplated. The tubing reservoir 64 provides the central portion 18 with additional capacity for the storage of medicated aerosol prior to inspiration by the patient.

A one-way valve 66 controls the flow of fluids (air, gas, aerosol, etc.) between the air inlet end portion 16 and the central portion 18. The valve 66 is identical in construction to the valves 42 and 58, and is disposed in the end portion 16 so that the flap 44 opens in the inspiratory direction indicated by the arrows 68. Thus, air may enter the central portion 18, but may not exit through the end portion 16.

Returning to the tee 56, which may also be provided with an eyelet 69 to facilitate suspension of the nebulizer 10 when not in use, a lower leg 70, also known as an aerosol outlet port, is connected to, and in fluid communication with, a connecting tube 72 which is integral with a cap 74. The tube 72 is fixed to the leg 70 so that the cap 74 is integrally joined to, and in fluid communication with, the tee 56. The cap 74 includes a top 76 having an upwardly projecting air inlet nipple 78 which is configured for connection to a source of air or oxygen which is pressurized in the range of 26 psi. (not shown). The cap 74 also includes a depending skirt 80 integral with a peripheral edge of the top 76. A plurality of spaced gripping ribs 82 are preferably provided on an outer surface of the skirt 80, and a helical thread 84 is preferably provided on an inner surface thereof (best seen in FIG. 2).

Referring now to FIG. 2, a medication reservoir or vial 86 is configured for connection to the tubular body 12 by means of threaded engagement with the cap 74. The vial 86 is preferably made of transparent polymeric plastic material and has an upper end 88 with a helical thread 90 for engagement with the thread 84 on the cap 74. In order to maximize efficient use of medication, the lower half 92 of the vial 86 tapers to form an inverted cone, and is graduated as shown at 94 for accurate measurement of medication.

A plurality (preferably four) of legs 96 are disposed on the lower half 92 of the vial 86 to enable the vial to be self-supporting on a table or other substrate while the medication is added. Although the vial 86 is preferably configured to have a generally conical lower tip or well 98, as an alternative, a bulb-shaped spherical tip 100 may be provided (shown in phantom in FIG. 2) to further maximize the utilization of the medication.

In order to avoid spillage of costly medications such as pentamidine, the vial 86 is provided with a frustoconically shaped spill-proof 102, which will also be referred to as a secondary baffle. The spill-proof 102 is preferably made of polymeric plastic material which is relatively flexible compared to the material used to make the vial 86 and the body 12, and is open at an upper end 104 as well as a lower end 106. The frustoconical shape of the spill-proof 102 causes an upper opening 108 to be larger in diameter than a lower opening 110. The lower opening 110 is preferably on the order of 0.750 to 0.850 inches in diameter, with 0.800 inches being preferred. The vertical distance between the upper and lower ends, 104, 106 respectively, is on the order of 0.650 to 0.700 inches, with 0.675 inches being preferred. The spill-proof 102 is releasably and sealingly secured to the upper end 88 of the vial 86 by an annular lip 111.

The nebulizer 10 includes a nebulizer jet mechanism generally designated 112, the general purpose of which is to create an aerosol of small particles of medication in the range of from 1 to 2 microns, and preferably between 1.5 and 2.5 microns from a mixture of medication from the vial 86 and gas, such as oxygen or air, from the inlet nipple 78. The nebulizer jet mechanism 112 includes a depending boss 114 integral with an underside 116 of the cap 74, and having a central throughbore 118 which is coaxial with the air inlet nipple 78. The throughbore 118 preferably has a lower end 120 which tapers to an opening 121 on the order of 0.020 inches.

A female jet member 122 includes an upper end 124 with a vertically projecting annular ring 126 defining a socket which sealingly and frictionally engages the boss 114 so as to create a relatively narrow mixing chamber 128. The socket defined by the annular ring 126 has a floor 130 with a jet orifice 132 which is coaxial with the throughbore 118 and generally codimensional with the opening 121 at the lower end 120. The floor 130 also has a depending siphon port 134 which is in fluid communication with the mixing chamber 128.

A siphon tube 136 made of relatively flexible polymeric plastic and having an inner diameter on the order of 0.045 to 0.055 inches is frictionally and sealingly engaged in the depending port 134. The diameter of the siphon tube 136 is selected to minimize the residual medication remaining in the vial 86 at the conclusion of the patient's treatment. The siphon tube 136 is long enough to extend to the area of the lower tip 98 of the vial 86. The female jet member 122 also includes a hemispherically-shaped primary baffle 138 integrally joined to the depending port 134 so as to be coaxial with the jet orifice 132.

In operation, oxygen or air is delivered under pressure into the inlet nipple 78, where it is passed through the throughbore 118, across the chamber 128 and through the jet orifice 132. The flow of oxygen in this manner, represented by the arrows 140, creates a suction in the siphon tube 136 through the Venturi effect, and draws medication, such as pentamidine, represented by the arrows 142 from the vial 86 and into the chamber 128. The medication mixes with the pressurized gas in the chamber 128 and is emitted as a mixture from the jet orifice 132. According to the Bernoulli effect, the pressure of the mixture will decrease upon emission from the jet orifice 132. The droplets of this mixture impact the primary baffle 138 and are initially fragmented into particles. The shape of the baffle 138 causes the particles to be directed in a radially outward pattern as indicated by the arrows 144. The initially fragmented particles will then be directed against the secondary baffle or spill-proof 102 for additional fragmentation.

After the second fragmentation, the particles will then fall through the lower opening 110 of the spill-proof 102 and will form an aerosol in the upper portion 88 of the vial 86 above the level of the medication. Despite the decrease in pressure of the incoming gas, the continual addition of gas/medication mixture to the upper portion 88 of the vial 86 will force the aerosol upward through the cap tube 72 and the aerosol outlet port 70, and into the central portion 18 of the tubular body 12. Through the circulation of the aerosol in the vial 86, the larger nebulized particles are trapped in the vial 86, and the finer particles migrate into the central portion 18. The aerosol will remain in this area due to the action of the one-way valves 58 and 66.

The mouthpiece 20 will be inserted into the patient's mouth. When the patient inhales, outside air is drawn through the air inlet end 16. The one-way valves 66 and 58 permit the incoming air, mixed with the stored dose of medicated aerosol to pass through the mouth piece 20 for inhalation by the patient. The valve 42 prevents any gas or aerosol from being diverted through the filter 34. The aerosol generated by the nebulizer 10 includes a significant proportion of particles in the optimum size range to maximize the amount of medication reaching the alveoli.

When the patient exhales, the exhalate may include aerosol, bacteria and viral elements, as well as carbon dioxide. Since pentamidine, as well as bacteria and viral elements, is toxic to health care workers and the environment, the nebulizer 10 prevents the emission of these undesirable products. The incoming flow of air from the mouthpiece 20 causes the flap 44 of the valve 58 to seat, thus sealing off the inspiratory end portion 14 from the rest of the nebulizer 10. This same flow of air forces the flap 44 of the valve 42 in an upward direction, permitting flow through the filter 34. The filter 34 operates to permit the flow of carbon dioxide through the outlet 41, but retains the unwanted respiratory byproducts. During the exhalation, the central portion 18 receives a new supply of aerosol for the next breathing cycle.

Thus, it will now be evident that the present nebulizer, incorporating the tubular body 12, the central portion 18 having one-way flow control valves 58 and 66, the filter 34 and the multi-baffled nebulizer jet mechanism 112, is designed to maximize the delivery of optimally-sized particles of medication such as pentamidine to the patient's alveoli.

While a particular embodiment of the nebulizer of the invention has been shown and described, it will be appreciated by those skilled in the art that changes and modifications may be made thereto without departing from the invention in its broader aspects and as set forth in the following claims.

What is claimed is:

1. A nebulizer for administering medicine to a patient, comprising:
   a tubular body having an inspiratory end portion, an opposing air inlet end portion and a central portion disposed between said inspiratory and said inlet end portions;
   a cap connected to said central portion and having a gas inlet nipple;
   one-way valve means for controlling the flow of fluid through said central portion from said inspiratory and said inlet end portions;
   a vial configured for connection to said cap and being in fluid communication with said central portion, said vial adapted to retain a supply of medicine therein;
   nebulizing means for creating an aerosol of the medicine, said nebulizing means including a plurality of baffle members and being disposed on said tubular body so as to be in fluid communication with said vial and said central portion;
   said nebulizing means further including a female jet member having an upper end with a vertically projecting annular ring defining a socket, said socket sealingly engaging a depending boss of said cap to define a mixing chamber having a jet orifice in a bottom surface thereof; a siphon port depending from said bottom surface and being in fluid communication with said mixing chamber; a primary baffle member integrally joined to said siphon port; a siphon tube engaged in said siphon port for drawing medicine from the vial; said mixing chamber adapted to receive gas from said inlet nipple and to mix the gas with medicine drawn through said siphon tube and to emit the mixture through said orifice; and
   said primary baffle disposed coaxially with said orifice and disposed in spaced relationship below said orifice to fragment droplets of the mixture emitted therefrom.

2. The nebulizer as defined in claim 1 wherein said primary baffle is hemispherical in shape.

3. The nebulizer as defined in claim 1 further including a secondary baffle.

4. The nebulizer as defined in claim 3 wherein said secondary baffle is disposed in an upper end of said vial.

5. The nebulizer as defined in claim 4 wherein said secondary baffle is frustoconical in shape with an open upper end in communication with said central portion and a tapered lower end, said lower end defining an opening.

6. The nebulizer as defined in claim 5 wherein said opening circumscribes said siphon tube.

7. The nebulizer as defined in claim 5 wherein said opening is on the order of 0.750 to 0.850 inches.

8. The nebulizer as defined in claim 5 wherein said secondary baffle is on the order of 0.650 to 0.700 inches in height.

9. The nebulizer as defined in claim 1 where said vial is configured to have a generally conical lower tip for maximum utilization of the medication.

10. A nebulizer for administering liquid respiratory medication to a patient, comprising:
   an elongate tubular body having an inspiratory end portion, an opposing air inlet end portion and a central portion disposed between said inspiratory and said inlet end portions;
   one-way valve means for controlling the flow of fluid through said central portion from said inspiratory and said inlet end portions;
   an aerosol inlet port depending from said central portion and having a cap with a port in fluid communication therewith, said cap having a gas inlet;
   a vial configured for releasable connection to said cap and being in fluid communication with said port, said vial adapted to retain a supply of medication therein;
   nebulizing means for creating an aerosol of the medicine, said nebulizing means including a jet orifice for emitting a pressurized mixture of gas from said gas inlet and medication from said vial in aerosol form, a primary baffle member disposed below said orifice to intercept and fragment the aerosol into particles, and a secondary baffle member circumscribing said primary baffle member to further intercept and fragment the aerosol;
   an upwardly projecting exhalatory port disposed on said tubular body portion between said central portion and said inspiratory end portion;
   filter means disposed upon an upper end of said exhalatory port; and
   one-way valve means for controlling the flow of fluid between said exhalatory port and said filter means.

11. The nebulizer as defined in claim 10 wherein said nebulizer means includes a female jet member having a siphon tube for drawing medicine from the vial, a gas inlet for receiving a supply of gas and being in fluid communication with said siphon tube, said jet orifice being in fluid communication with said gas inlet.

12. The nebulizer as defined in claim 10 wherein said primary baffle is hemispherical in shape.

13. The nebulizer as defined in claim 11 wherein said primary baffle is integral with said female jet member.

14. The nebulizer as defined in claim 10 wherein said secondary baffle is disposed in an upper end of said vial.

15. The nebulizer as defined in claim 14, wherein said secondary baffle is frustoconical in shape with an open upper end and a tapered lower end, said lower end defining an opening, said opening adapted to circumscribe said siphon tube.

16. A nebulizer for administering medicine to a patient, comprising:
   a tubular body having an inspiratory end portion, an opposing air inlet end portion and a central portion disposed between said inspiratory and said inlet end portions;
   a cap connected to said central portion and having a gas inlet nipple;
   a vial configured for connection to said cap and being in fluid communication with said central portion, said vial adapted to retain a supply of medicine therein;
   one-way valve means for controlling the flow of fluid through said central portion from said inspiratory and said inlet end portions, said one way valve means including a plurality of one way valves disposed in said body to define an enclosed chamber in said central portion of said tubular body where an amount of medicated aerosol can be stored between inhalations;
   nebulizing means for creating an aerosol of the medicine, said nebulizing means including a plurality of baffle members and being disposed on said tubular body so as to be in fluid communication with said vial and said central portion;
   said nebulizing means further including a female jet member configured to sealingly engage a depending boss of said cap to define a mixing chamber, said jet member also having a siphon tube for drawing medicine from the vial into said chamber, a gas inlet for receiving gas from said nipple, and a jet orifice for emitting a mixture of medicine and gas, a primary baffle member integrally joined to said siphon port disposed coaxially with said orifice and disposed in spaced relationship below said orifice to fragment droplets of the mixture emitted therefrom;
   an upwardly projecting exhalatory port disposed on said tubular body portion between said central portion and said inspiratory end portion;
   filter means disposed upon an upper end of said exhalatory port; and
   second one-way valve means for controlling the flow of fluid between said exhalatory port and said filter means;
   wherein said chamber is isolated by said first and second one-way valve means valves so that gas exhaled by the patient passes only through said exhalatory port and said filter means.

17. The nebulizer as defined in claim 16 further comprising a secondary frustoconical baffle with an upper end, and a lower end defining an opening circumscribing said siphon tube, said secondary baffle being disposed in an upper end of said vial.

18. The nebulizer as defined in claim 16 wherein said vial has a bulb-shaped spherical tip for maximum utilization of the medication.

* * * * *

UNITED STATES PATENT AND TRADEMARK OFFICE
CERTIFICATE OF CORRECTION

PATENT NO. : 5,086,765

DATED : February 11, 1992

INVENTOR(S) : Walter Levine

It is certified that error appears in the above-identified patent and that said Letters Patent is hereby corrected as shown below:

On cover page, column 2, after the line "Assistant Examiner - Lisa Malvaso"

insert the line

--Attorney, Agent, or Firm - Welsh & Katz, Ltd.--.

Signed and Sealed this

Thirteenth Day of April, 1993

Attest:

STEPHEN G. KUNIN

*Attesting Officer*  Acting Commissioner of Patents and Trademarks